June 8, 1954 B. J. ROKOS Plant Pat. 1,282
ROSE PLANT
Filed Nov. 10, 1951
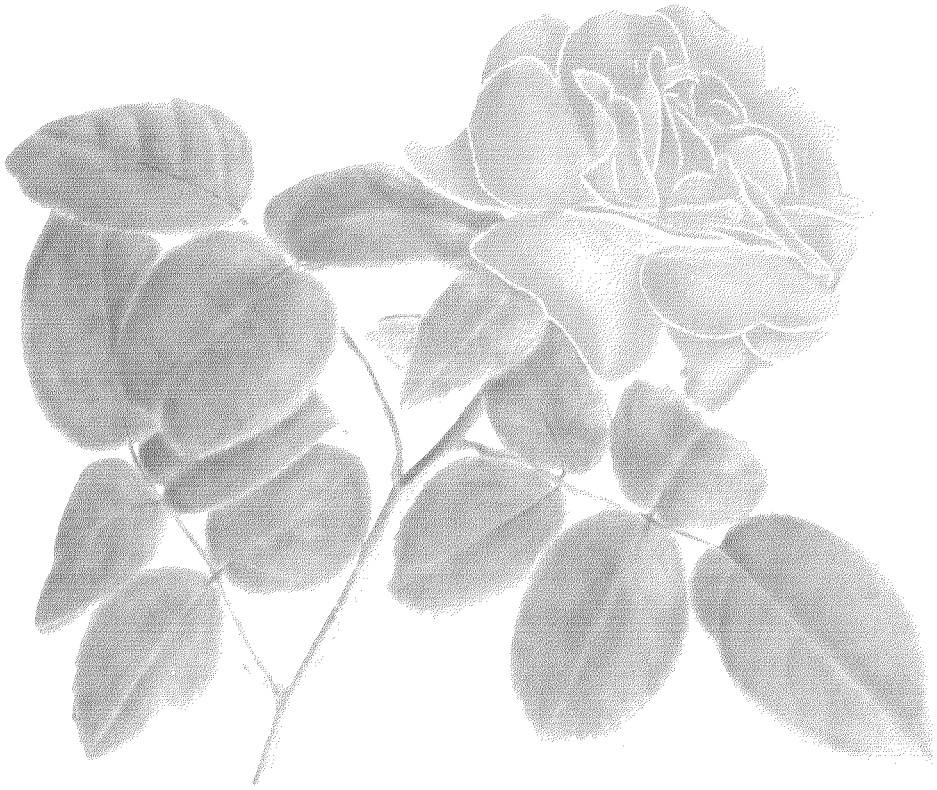
INVENTOR
BOGUSTUS J. ROKOS
BY Norman J. Hughes
ATTORNEY Patented June 8, 1954

Plant Pat. 1,282

UNITED STATES PATENT OFFICE 1,282

ROSE PLANT

Bogustus J. Rokos, Detroit, Mich.

Application November 10, 1951, Serial No. 255,801

1 Claim. (Cl. 47—61)

My present discovery relates to a new and distinctive type of hybrid tea rose plant characterized principally by the combination of flowers of a dominating Light Jasper Red color with the center of the bloom or base portions of the petals a Primuline Yellow and with the petals having a white edging.

My new variety of rose plant originated as a sport of the "Peace" rose, Plant Patent 591, and was discovered by me several years ago in my small cultivated garden owned and controlled by me and located just to the rear of my place of residence in Detroit, Michigan. In the spring of 1948 I had growing in my garden aforesaid a splendid hybrid tea rose plant from which I cut a branch and propagated in that garden five separate cuttings therefrom. Four of these upon growth were identical in every respect with the parent plant, but the fifth one had embodied therein the distinct color characteristics as shown in the accompanying drawings and as hereinafter described and claimed. It has been asexually reproduced since that time by my taking several cuttings therefrom and planting each cutting separately and propagating the same and its features appear to be firmly fixed. This asexual reproduction was done at Detroit, Michigan.

The accompanying illustration shows, in color, the flower in full bloom and its leaves and stem.

The new and distinct variety of rose embodying this invention is characterized by the following:

The rose of this invention is substantially identical with the rose "Peace" in its form, shape of leaves, thorniness, habits of growth, profusion and periods of bloom.

The buds of the rose of this invention, and also the open blooms, are substantially of the same size and shape as those of the parent, but the rose of this invention is distinguishable therefrom by its colors aforesaid and its heavier and pleasantly stronger aroma. Moreover the buds and flower of the rose of this invention maintain the same colorings throughout their lives.

The colors of the rose of my invention, as herein referred to, are given by reference to Color Standards and Nomenclature, Ridgway (Copy. 1912). Thus in the drawing accompanying this application the flower is shown in full bloom. The outer edge of each petal is white, or in other words, the petals have thin white border lines. The coloring of the major portion of the petal from the white border inwardly is Light Jasper Red (Plate XIII) shading to a Primuline Yellow (Plate XVI) at its base.

I claim:

The new and distinct variety of rose plant as described and illustrated, characterized as to novelty by the shadings of the petals of the flowers which are white at their edges and a Light Jasper Red inwardly therefrom, shading to a Primuline Yellow at their bases.

No reference cited.